US00PP10076P

United States Patent [19]

Wain

[11] Patent Number: Plant 0,076

[45] Date of Patent: Oct. 21, 1997

[54] CHRYSANTHEMUM PLANT NAMED 'FIJI'

[75] Inventor: Peter Wain, Hayling Island, United Kingdom

[73] Assignee: Cleangro Ltd., Chichester, United Kingdom

[21] Appl. No.: 648,930

[22] Filed: May 16, 1996

[51] Int. Cl.[6] ..... A01H 5/00

[52] U.S. Cl. ..... Plt./80

[58] Field of Search ..... Plt./76, 80, 81

[56] References Cited

U.S. PATENT DOCUMENTS

P.P. 3,401 9/1973 Machin ..... Plt./77

*Primary Examiner*—Howard J. Locker

*Attorney, Agent, or Firm*—C. A. Whealy

[57] ABSTRACT

A distinct cultivar of Chrysanthemum plant named Fiji, characterized by its flat capitulum form; decorative-type inflorescences; early flowering; light pink ray florets; numerous inflorescences per plant when grown as a spray; numerous ray florets per inflorescence; and strong peduncles and stems.

1 Drawing Sheet

The present invention relates to a new and distinct cultivar of Chrysanthemum plant, botanically known as *Dendranthema grandiflora* and referred to by the cultivar name Fiji.

The new cultivar is a product of a planned breeding program conducted by the inventor in Havant, Hampshire, United Kingdom. The objective of the breeding program was to create new Chrysanthemum cultivars having strong stems and peduncles, desirable inflorescence colors, and that develop inflorescences quickly.

The new cultivar originated from a cross made by the inventor of the inventor's proprietary Chrysanthemum selection code number 7GJ as the male or pollen parent with the Chrysanthemum cultivar Snowdon (disclosed in U.S. Plant Pat. No. 3,401), a white cut Chrysanthemum, as the female or seed parent.

The cultivar Fiji was discovered and selected by the inventor as a flowering plant within the progeny of the stated cross in a controlled environment in Havant, Hampshire, United Kingdom.

Asexual reproduction of the new cultivar by terminal cuttings taken at Havant, Hampshire, United Kingdom, has shown that the unique features of this new Chrysanthemum are stable and reproduced true to type in successive generations.

The following traits have been repeatedly observed and are determined to be the unique characteristics of Fiji. These characteristics in combination distinguish Fiji as a new and distinct cultivar:

1. Flat capitulum form.
2. Decorative-type inflorescences.
3. Can be produced as a spray or standard cut Chrysanthemum.
4. Flowers after exposure to about eight weeks of short days.
5. Light pink ray florets.
6. Numerous inflorescences per plant when grown as a spray.
7. Numerous ray florets per inflorescence.
8. Strong peduncles and stems.

The cultivar Fiji has not been observed under all possible environmental conditions. The phenotype may vary somewhat with variations in environment such as temperature, daylength and light intensity, without, however, any variance in genotype.

In side-by-side comparisons in Havant, Hampshire, United Kingdom, under commercial practice, plants of the new Chrysanthemum have larger inflorescences that are lighter pink color compared to plants of the male parent, the proprietary selection 7GJ. Plants of the new Chrysanthemum primarily differ from the female parent, the Chrysanthemum cultivar Snowdon, in ray floret color.

Plants of the new Chrysanthemum are similar to the cultivar Dolly (not patented). However, in side-by-side comparisons conducted in Oxnard, Calif., under commercial practice, plants of the new Chrysanthemum differed from plants of the cultivar Dolly in the following characteristics:

1. Plants of the new Chrysanthemum have longer and narrower leaves than plants of the cultivar Dolly.
2. Plants of the new Chrysanthemum have longer leaf petioles than plants of the cultivar Dolly.
3. Plants of the new Chrysanthemum have larger inflorescences than plants of the cultivar Dolly.
4. Ray florets of plants of the new Chrysanthemum are deeper pink than ray florets of plants of the cultivar Dolly.
5. Ray florets of plants of the new Chrysanthemum are cupped whereas ray florets of plants of the cultivar Dolly are flat.
6. The lower peduncles of plants of the new Chrysanthemum are shorter than the lower peduncles of plants of the cultivar Dolly.

The accompanying colored photograph illustrates the overall appearance of the new cultivar, showing the colors as true as it is reasonably possible to obtain in colored reproductions of this type. The photograph comprises a side perspective view of a typical flowering stem of Fiji grown as a spray (terminal inflorescence removed).

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with average night temperatures of 18C, average day temperatures of 24C, and light levels ranging from 2,000 (cloudy conditions) to 8,000 (sun conditions) footcandles.

After sticking unrooted cuttings of the new cultivar in early January, plants received 14 long day/short nights followed by short day/long nights until flowering in mid-March. Immature terminal inflorescences were removed and flowering stems were grown as sprays. Measurements and numerical values represent ranges or averages for six typical flowering stems.

Botanical classification: *Dendranthema grandiflora* cultivar Fiji.

Commercial classification: Decorative cut Chrysanthemum.

Parentage:

*Male, or pollen, parent.*—Proprietary selection code number 7GJ.

*Female, or seed, parent.*—*Dendranthema grandiflora* cultivar Snowdon (disclosed in U.S. Plant Pat. No. 3,401).

Propagation:

*Type.*—Terminal tip cuttings.

*Time to rooting.*—7 to 10 days with soil temperatures of 22C.

*Rooting habit.*—Fine, fibrous and well-branched.

Plant description:

*Appearance.*—Perennial herbaceous decorative-type cut flower. Stems upright, uniform habit and freely branching. Can be grown as a spray (center bud removed) or as a standard (lateral buds removed). Flowering stem length is about 80 cm.

*Vigor.*—Moderate.

*Foliage description.*—Leaf arrangement: Alternate. Leaf size, fully expanded: Length: 11.5 to 12.5 cm. Width: 5.5 to 7 cm. Leaf apex: Acuminate. Leaf base: Attenuate. Leaf margin: Palmately lobed. Leaf texture: Upper and under surfaces slightly pubescent. Veins prominent on under surface. Petiole length: 2.5 to 3 cm. Color: Young foliage upper surface: 147A. Young foliage under surface: 147B. Mature foliage upper surface: 147A. Mature foliage under surface: 147B. Venation upper surface: 147B. Venation under surface: 147B. Petiole: 147A.

Flowering description:

*Appearance.*—Decorative inflorescence form. Inflorescences borne on terminals above foliage. Florets arranged acropetally on a flat capitulum. Can be grown as a spray or as a standard.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to about 2 weeks of long day/short night conditions after planting followed by photoinductive short day/long night conditions, flower about 54 days later.

*Quantity of inflorescences.*—10 to 12 inflorescences per flowering stem.

*Bud.*—Size, showing color: Length: About 1 cm. Width: About 1 cm. Color: 155D becoming pink, 62D, as inflorescence develops.

*Inflorescence size.*—Diameter: 8 to 9 cm. Depth (height): 1.5 to 1.7 cm.

*Ray florets.*—Shape: Elongated. Size: Length: 4 to 4.4 cm. Width: 1.3 to 1.5 cm. Apex: variable, slightly dentate to rounded. Base: Acute. Margin: Entire. Texture: Satiny, smooth, glabrous, ribbed lengthwise. Aspect: Cupped. Number of ray florets per inflorescence: About 237. Color: When opening, upper surface: 155D. When opening, under surface: 62D. Mature, upper surface: 62C and slightly darker 62B, at base. Color fades to 62D with further development. Mature, under surface: 62D. Color does not fade with further development.

*Disc florets.*—Shape: Tubular. Size: Length: About 2 mm. Width: About 1 mm. Number of disc florets per inflorescence: About 12. Color: Immature: 154A. Mature: 12A.

*Peduncle.*—Aspect: Strong. Length: First peduncle: 6 to 8 cm. Fourth peduncle: 8.5 to 9 cm. Texture: Glabrous. Color: 137B.

*Reproductive organs.*—Androecium: Present on disc florets only. Anther color: 12A. Pollen: Moderate, 12 A in color. Gynoecium: Present on both ray and disc florets. Style color: 154A.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named Fiji, as illustrated and described.

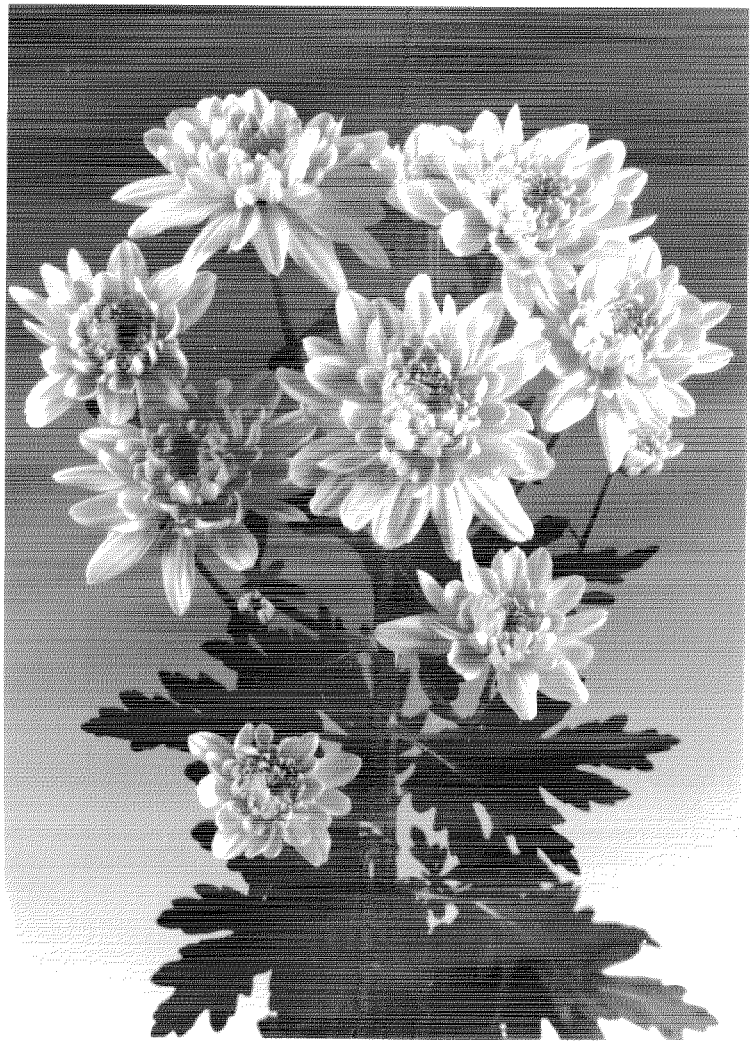

* * * * *